US 7,087,263 B2

(12) United States Patent
Hossainy et al.

(10) Patent No.: US 7,087,263 B2
(45) Date of Patent: *Aug. 8, 2006

(54) RARE LIMITING BARRIERS FOR IMPLANTABLE MEDICAL DEVICES

(75) Inventors: Syed F A Hossainy, Fremont, CA (US); Fuh-Wei Tang, Temecula, CA (US); Houdin Dehnad, El Granada, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 582 days.

This patent is subject to a terminal disclaimer.

(21) Appl. No.: 10/269,004

(22) Filed: Oct. 9, 2002

(65) Prior Publication Data

US 2004/0072922 A1    Apr. 15, 2004

(51) Int. Cl.
*A61L 33/00*     (2006.01)
*A61K 9/00*      (2006.01)
*A61K 47/32*     (2006.01)

(52) U.S. Cl. .................... 427/2.1; 424/400; 514/772.4

(58) Field of Classification Search ............. 514/772.4; 424/400; 427/2.1
See application file for complete search history.

(56) References Cited

U.S. PATENT DOCUMENTS

| | | | |
|---|---|---|---|
| 2,072,303 A | 3/1937 | Herrmann et al. ........ 128/335.5 |
| 4,329,383 A | 5/1982 | Joh ............................ 428/36 |
| 4,733,665 A | 3/1988 | Palmaz ...................... 128/343 |
| 4,800,882 A | 1/1989 | Gianturco ................... 128/343 |
| 4,882,168 A | 11/1989 | Casey et al. ................ 424/468 |
| 4,886,062 A | 12/1989 | Wiktor ...................... 128/343 |
| 4,941,870 A | 7/1990 | Okada et al. ................. 600/36 |
| 4,977,901 A | 12/1990 | Ofstead ..................... 128/772 |
| 5,112,457 A | 5/1992 | Marchant .................... 204/165 |
| 5,165,919 A | 11/1992 | Sasaki et al. ............... 424/488 |
| 5,272,012 A | 12/1993 | Opolski ................... 428/423.1 |
| 5,292,516 A | 3/1994 | Viegas et al. ............... 424/423 |
| 5,298,260 A | 3/1994 | Viegas et al. ............... 424/486 |
| 5,300,295 A | 4/1994 | Viegas et al. ............... 424/427 |
| 5,306,501 A | 4/1994 | Viegas et al. ............... 424/423 |
| 5,328,471 A | 7/1994 | Slepian ....................... 604/101 |
| 5,330,768 A | 7/1994 | Park et al. ................... 424/501 |
| 5,380,299 A | 1/1995 | Fearnot et al. .............. 604/265 |
| 5,417,981 A | 5/1995 | Endo et al. .................. 424/486 |
| 5,447,724 A | 9/1995 | Helmus et al. .............. 424/426 |
| 5,455,040 A | 10/1995 | Marchant .................... 424/426 |
| 5,462,990 A | 10/1995 | Hubbell et al. .............. 525/54.1 |
| 5,464,650 A | 11/1995 | Berg et al. ................... 427/2.3 |
| 5,569,463 A | 10/1996 | Helmus et al. .............. 424/426 |
| 5,578,073 A | 11/1996 | Haimovich et al. ............ 623/1 |
| 5,605,696 A | 2/1997 | Eury et al. .................. 424/423 |
| 5,609,629 A | 3/1997 | Fearnot et al. ................ 623/1 |
| 5,624,411 A | 4/1997 | Tuch ......................... 604/265 |
| 5,628,730 A | 5/1997 | Shapland et al. .............. 604/21 |
| 5,649,977 A | 7/1997 | Campbell .................... 623/1 |
| 5,658,995 A | 8/1997 | Kohn et al. .................. 525/432 |
| 5,667,767 A | 9/1997 | Greff et al. .............. 424/9.411 |
| 5,670,558 A | 9/1997 | Onishi et al. ................ 523/112 |
| 5,679,400 A | 10/1997 | Tuch ......................... 427/2.14 |
| 5,700,286 A | 12/1997 | Tartaglia et al. ................ 623/1 |
| 5,702,754 A | 12/1997 | Zhong ....................... 427/2.12 |
| 5,716,981 A | 2/1998 | Hunter et al. ............... 514/449 |
| 5,735,897 A | 4/1998 | Buirge ......................... 623/12 |
| 5,746,998 A | 5/1998 | Torchilin et al. ............ 424/9.4 |
| 5,776,184 A | 7/1998 | Tuch ............................ 623/1 |
| 5,788,979 A | 8/1998 | Alt et al. ..................... 424/426 |
| 5,800,392 A | 9/1998 | Racchini ...................... 604/96 |
| 5,820,917 A | 10/1998 | Tuch ......................... 427/2.1 |
| 5,824,048 A | 10/1998 | Tuch ............................ 623/1 |
| 5,824,049 A | 10/1998 | Ragheb et al. ................. 623/1 |
| 5,830,178 A | 11/1998 | Jones et al. ................... 604/49 |
| 5,837,008 A | 11/1998 | Berg et al. ..................... 623/1 |
| 5,837,313 A | 11/1998 | Ding et al. ................. 427/2.21 |
| 5,851,508 A | 12/1998 | Greff et al. .............. 424/9.411 |
| 5,852,114 A * | 12/1998 | Loomis et al. |
| 5,858,746 A | 1/1999 | Hubbell et al. ............. 435/177 |
| 5,865,814 A | 2/1999 | Tuch ......................... 604/265 |
| 5,869,127 A | 2/1999 | Zhong ....................... 427/2.12 |
| 5,873,904 A | 2/1999 | Ragheb et al. ................. 623/1 |
| 5,876,433 A | 3/1999 | Lunn ............................ 623/1 |
| 5,877,224 A | 3/1999 | Brocchini et al. ........ 514/772.2 |
| 5,925,720 A | 7/1999 | Kataoka et al. ............. 525/523 |
| 5,955,509 A | 9/1999 | Webber et al. ........... 514/772.7 |
| 5,971,954 A | 10/1999 | Conway et al. ............... 604/96 |
| 5,980,928 A | 11/1999 | Terry ......................... 424/427 |
| 5,980,972 A | 11/1999 | Ding ......................... 427/2.24 |
| 5,997,517 A | 12/1999 | Whitbourne ................ 604/265 |
| 6,010,530 A | 1/2000 | Goicoechea ................... 623/1 |
| 6,015,541 A | 1/2000 | Greff et al. ................ 424/1.25 |
| 6,033,582 A | 3/2000 | Lee et al. ...................... 216/37 |
| 6,042,875 A | 3/2000 | Ding et al. ................. 427/2.24 |
| 6,051,576 A | 4/2000 | Ashton et al. .............. 514/255 |
| 6,051,648 A | 4/2000 | Rhee et al. ................. 525/54.1 |
| 6,056,993 A | 5/2000 | Leidner et al. ............. 427/2.25 |

(Continued)

FOREIGN PATENT DOCUMENTS

EP    0 301 856    2/1989

(Continued)

OTHER PUBLICATIONS

U.S. Appl. No. 09/621,123, filed Jul. 21, 2000, Bhat et al.

(Continued)

*Primary Examiner*—Humera N. Sheikh
(74) *Attorney, Agent, or Firm*—Squire, Sanders & Dempsey, L.L.P.

(57) ABSTRACT

A coating for a medical device, particularly for a drug eluting stent, is described. The coating comprises a polymer having a weight-average molecular weight between about 200,000 and about 250,000 Daltons or a polydispersity index between about 2.6 and about 3.0.

22 Claims, No Drawings

U.S. PATENT DOCUMENTS

| | | | |
|---|---|---|---|
| 6,060,451 A | 5/2000 | DiMaio et al. ............... 514/13 |
| 6,060,518 A | 5/2000 | Kabanov et al. ............ 514/781 |
| 6,080,488 A | 6/2000 | Hostettler et al. ........ 428/423.3 |
| 6,096,070 A | 8/2000 | Ragheb et al. ................. 623/1 |
| 6,099,562 A | 8/2000 | Ding et al. ............... 623/1.46 |
| 6,110,188 A | 8/2000 | Narciso, Jr. ................. 606/153 |
| 6,110,483 A | 8/2000 | Whitbourne et al. ....... 424/423 |
| 6,113,629 A | 9/2000 | Ken ............................. 623/1.1 |
| 6,120,536 A | 9/2000 | Ding et al. ............... 623/1.43 |
| 6,120,904 A | 9/2000 | Hostettler et al. ........ 428/423.3 |
| 6,121,027 A | 9/2000 | Clapper et al. ............. 435/180 |
| 6,129,761 A | 10/2000 | Hubbell ....................... 623/11 |
| 6,153,252 A | 11/2000 | Hossainy et al. ............ 427/2.3 |
| 6,165,212 A | 12/2000 | Dereume et al. .......... 623/1.13 |
| 6,203,551 B1 | 3/2001 | Wu ............................. 606/108 |
| 6,231,600 B1 | 5/2001 | Zhong ....................... 623/1.42 |
| 6,240,616 B1 | 6/2001 | Yan ........................... 29/527.2 |
| 6,245,753 B1 | 6/2001 | Byun et al. .................... 514/56 |
| 6,251,136 B1 | 6/2001 | Guruwaiya et al. ........ 623/1.46 |
| 6,254,632 B1 | 7/2001 | Wu et al. .................. 623/1.15 |
| 6,258,121 B1 | 7/2001 | Yang et al. ................ 623/1.46 |
| 6,283,947 B1 | 9/2001 | Mirzaee ...................... 604/264 |
| 6,283,949 B1 | 9/2001 | Roorda .................. 604/288.02 |
| 6,284,305 B1 | 9/2001 | Ding et al. ................ 427/2.28 |
| 6,287,628 B1 | 9/2001 | Hossainy et al. ............ 427/2.3 |
| 6,299,604 B1 | 10/2001 | Ragheb et al. ............... 604/265 |
| 6,306,176 B1 | 10/2001 | Whitbourne ............ 623/23.59 |
| 6,331,313 B1 | 12/2001 | Wong et al. ................. 424/427 |
| 6,335,029 B1 | 1/2002 | Kamath et al. ............. 424/423 |
| 6,346,110 B1 | 2/2002 | Wu ............................. 606/108 |
| 6,358,556 B1 | 3/2002 | Ding et al. ................ 427/2.24 |
| 6,379,381 B1 | 4/2002 | Hossainy et al. .......... 623/1.42 |
| 6,395,326 B1 | 5/2002 | Castro et al. ............. 427/2.24 |
| 6,419,692 B1 | 7/2002 | Yang et al. ................ 623/1.15 |
| 6,451,373 B1 | 9/2002 | Hossainy et al. .......... 427/2.25 |
| 6,494,862 B1 | 12/2002 | Ray et al. ................. 604/96.01 |
| 6,503,556 B1 | 1/2003 | Harish et al. .............. 427/2.24 |
| 6,503,954 B1 | 1/2003 | Bhat et al. ................ 514/772.2 |
| 6,506,437 B1 | 1/2003 | Harish et al. .............. 427/2.25 |
| 6,527,801 B1 | 3/2003 | Dutta ........................ 623/1.46 |
| 6,527,863 B1 | 3/2003 | Pacetti et al. ............... 118/500 |
| 6,540,776 B1 | 4/2003 | Sanders Millare et al. 623/1.15 |
| 6,544,223 B1 | 4/2003 | Kokish ................... 604/103.01 |
| 6,544,543 B1 | 4/2003 | Mandrusov et al. ........ 424/422 |
| 6,544,582 B1 | 4/2003 | Yoe ............................ 427/2.24 |
| 6,555,157 B1 | 4/2003 | Hossainy .................... 427/2.24 |
| 6,558,733 B1 | 5/2003 | Hossainy et al. .......... 427/2.24 |
| 6,565,659 B1 | 5/2003 | Pacetti et al. ............... 118/500 |
| 6,572,644 B1 | 6/2003 | Moein ........................ 623/1.11 |
| 6,585,765 B1 | 7/2003 | Hossainy et al. .......... 623/1.45 |
| 6,585,926 B1 | 7/2003 | Mirzaee ...................... 264/400 |
| 6,605,154 B1 | 8/2003 | Villareal ..................... 118/500 |
| 6,713,119 B1 * | 3/2004 | Hossainy et al. |
| 6,818,247 B1 * | 11/2004 | Chen et al. |
| 2001/0018469 A1 | 8/2001 | Chen et al. .................. 523/121 |
| 2001/0037145 A1 | 11/2001 | Guruwaiya et al. |
| 2002/0077693 A1 | 6/2002 | Barclay et al. ............ 623/1.13 |
| 2002/0091433 A1 | 7/2002 | Ding et al. .................. 623/1.2 |
| 2002/0123788 A1 | 9/2002 | Sanders Millare et al. 623/1.13 |
| 2002/0155212 A1 | 10/2002 | Hossainy ................... 427/2.25 |
| 2003/0065377 A1 | 4/2003 | Davila et al. ............. 623/1.13 |
| 2003/0099712 A1 | 5/2003 | Jayaraman ................. 424/486 |

FOREIGN PATENT DOCUMENTS

| | | |
|---|---|---|
| EP | 0 310 856 | 2/1989 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 734 721 | 10/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | 01/45763 A1 * | 6/2001 |
| WO | WO 01/45763 | 6/2001 |
| WO | WO 01/49338 | 7/2001 |
| WO | WO 01/53414 | 7/2001 |
| WO | WO 01/74414 | 10/2001 |
| WO | WO 02/03890 | 1/2002 |
| WO | WO 02/026162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Rolling Therapeutic Agent Loading Device for Therapeutic Agent Delivery or Coated Stent* (Abstract 434009), Res. Disclos. p. 975 (Jun. 2000).

Barath et al; *Low Dose of Antitumor Agents Prevents Smooth Muscle Cell Proliferation After Endothelial Injury* JCAA 13(2):252A (1989).

Dichek et al., *Seeding of Intravascular Stents with Genetically Engineered Endothelial Cells*, Circ. 80(5):1347-1353 (1989).

Herdeg et al., *Antiproliferative Stent Coatings: Taxol and Related Compounds*, Semin. Intervent. Cardiol. 3:197-199 (1998).

Matsumaru et al.; *Embolic Materials for Endovascular Treatment of Cerebral Lesions*, J. Biomater. Sci. Polymer Edn. 8(7):555-569 (1997).

Miyazaki et al.; *Antitumor effect of Implanted Ethylene-Vinyl Alcohol Copolymer Matrices Containing Anticancer Agents on Ehrlich Ascites Carcinoma and P388 Leukemia in Mice;* Chem. Pharm. Bull. 33(6):2490-2498 (1985).

Miyazawa et al.; *Effects of Pemirolast and Tranilast on Intimal Thickening After Arterial Injury in the Rat*; J. Cardiovasc. Pharmacol., pp. 157-162 (1997).

Ohsawa et al.; *Preventive Effects of an Antiallergic Drug, Pemirolast Potassium, on Restenosis After Percutaneous*

*Transluminal Coronary Angioplasty*; American Heart Journal; pp. 1081-1087 (1998).

Shigeno; *Prevention of Cerebrovascular Spasm By Bosentan, Novel Endothelin Receptor*, Chemical Abstract 125:212307 (1996).

Anonymous, *Cardiologists Draw —Up The Dream Stent*, Clinica 710:15 (Jun. 17, 1996), http://www.dialogweb.com/cgi/document?req=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Inoue et al., *An AB block copolymer of oligo(methyl methacrylate)and poly(acrylic acid)for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Nordrehaug et al., *A novel biocompatible coating applied to coronary stents*, European Heart Journal 14, p. 321 (P1694), Abstr. Suppl. (1993).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

RARE LIMITING BARRIERS FOR IMPLANTABLE MEDICAL DEVICES

BACKGROUND OF THE INVENTION

1. Field of the Invention

This invention is directed to coatings for implantable medical devices, such as stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents described in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for local administration of a therapeutic substance at the diseased site. In order to provide an efficacious concentration to the treatment site, systemic administration of such medication often leads to adverse or toxic side effects on the patient. Local delivery is a preferred method of treatment in that, in comparison to systemic dosages, smaller total levels of medication can be administered but are concentrated at a specific site. Local delivery thus produces fewer side effects and achieves better results. One proposed method for medicating stents involves the use of a polymeric carrier coated onto the surface of a stent. A blend which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

To the extent that the mechanical functionality of stents has been optimized in recent years, continued improvements in the local delivery of drugs by a stent is needed. More specifically, for effective treatment of restenosis, it is important to maintain the concentration of the drug at a therapeutically effective level for a period of time. Hence, controlling a rate of release of the drug from the stent coating is important. In view of the foregoing, coatings for reducing the rate of release of a therapeutic substance from implantable devices, such as stents, are desired.

SUMMARY

According to one embodiment of this invention, a coating for an implantable medical device is provided, the coating comprises poly(ethylene-co-vinyl alcohol) having a weight-average molecular weight between about 200,000 and about 250,000 Daltons.

According to another embodiment of this invention, a coating for an implantable medical device is provided, the coating comprising poly(ethylene-co-vinyl alcohol) having a polydispersity index between about 2.6 and about 3.0.

According to yet another embodiment of the invention, a coating for an implantable medical device is provided, the coating comprising a first layer containing a polymer and a therapeutic substance, wherein a ratio of the therapeutic substance to the polymer in the first layer is between about 1:1 and about 1:25.

According to yet another embodiment of the invention, a method of coating a stent is provided, the method comprising forming a coating comprising a copolymer of ethylene and vinyl alcohol on the stent, the copolymer having a weight-average molecular weight between about 200,000 and about 250,000 Daltons or a polydispersity index between about 2.6 and about 3.0.

DETAILED DESCRIPTION

A coating for an implantable medical device, such as a stent, can include a drug-polymer layer, a topcoat layer, and an optional primer and finishing coat layers. The drug-polymer layer can be applied directly onto the stent and to serve as a reservoir for sustained release of a therapeutic agent. The topcoat layer serves as a rate limiting membrane which controls the rate of release of the therapeutic agent. The optional primer layer can be applied between the stent and the drug-polymer layer to improve the adhesion of the coating to the stent. An optional finishing coat layer can be applied over the topcoat layer and can serve as the outermost layer of the coating. The finishing coat layer can be used for improving the biocompatibility of the underlying layer.

The process of the release of a drug includes at least three distinctive steps. First, the drug is absorbed by the polymer of the topcoat layer on the drug-polymer layer/topcoat layer interface. Next, the drug diffuses through the topcoat layer using empty spaces between the macromolecules of the topcoat layer polymer as pathways for migration. Finally, the drug arrives to the outer surface of the topcoat layer and desorbs from the outer surface. At this point, the drug is released into the blood stream. If the finishing coat layer is used, the drug can diffuse through the finishing coat layer in a similar fashion. Therefore, an optional finishing coat layer, if used, can also serve as a rate limiting barrier.

According to one embodiment of the present invention, a topcoat layer having properties is formed to provide an enhanced degree of control of the rate of release of the drug. The topcoat layer can be made of a polymer having an increased weight-average molecular weight ($M_w$), or an increased value of the polydispersity index (PDI), or both increased $M_w$ and the PDI value. For the purposes of the present invention, the term "increased" is used in reference to the $M_w$ and/or the PDI value of the polymers currently used to make the topcoat layer.

Synthetic and natural polymers have a distribution of molecular weights. The PDI, also known as the molecular weight distribution (MWD), is a ratio between $M_w$ and the number-average molecular weight ($M_n$). The $M_w/M_n$ ratio has been classically used to define the breadth of the distribution of the molecular weight. $M_n$ depends on a counting procedure and is commonly measured by osmometry yields, while $M_w$ measures the weight. Light-scattering techniques are typically used to determine $M_w$.

A copolymer of ethylene and vinyl alcohol (EVAL) is one example of a polymer used to fabricate the optional primer layer, the drug-polymer layer, the topcoat layer and/or the finishing coat layer. EVAL has the general formula —[CH$_2$—CH$_2$]$_m$—[CH$_2$—CH(OH)]$_n$—. EVAL is a product of hydrolysis of ethylene-vinyl acetate copolymers and may also be a terpolymer including up to 5 molar % units derived from styrene, propylene and other suitable unsaturated monomers. A brand of copolymer of ethylene and vinyl alcohol which is commercially available, e.g., under the trade name EVAL by Aldrich Chemical Co. of Milwaukee, Wis., and manufactured by EVAL Company of America of Lisle, Ill., can be used.

In one embodiment, the topcoat layer can be made of a brand of EVAL having an $M_w$ of between about 200,000 and about 250,000. In another embodiment, the EVAL can have the PDI value of between about 2.6 and 3.0. In yet another embodiment, the EVAL can have both an $M_w$ of between about 200,000 and about 250,000 and he a PDI value of between about 2.6 and 3.0. Theses ranges of $M_w$ and/or the PDI are expected to result in a decrease of in the release rate of a drug in the coating. A grade of EVAL having $M_w$ of between about 160,000 and about 180,000 and the PDI— between about 2.2 and 2.4 can be used to make the optional primer layer and/or the drug-polymer layer.

Other suitable polymers can also be used to form the optional primer layer, the drug-polymer layer, the topcoat layer, and/or the optional finishing coat layer. For any selected polymer, those having ordinary skill in the art will choose most appropriate $M_w$ and the PDI. Representative examples of suitable polymers include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane; poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

According to another embodiment of the present invention, release rate of a drug in a coating can be modulated by adjusting the ratio between the drug and the polymer in the drug-polymer layer of the stent coating. In accordance with the present invention, the ratio can be between about 1:1 and about 1:25, for example, about 1:1.25. The coating can have a single drug-polymer layer or a plurality of sequentially applied drug-polymer sub-layers, where each drug-polymer sub-layer can have a different ratio between the drug and the polymer within the 1:1 to 1:25 limits. The drugs contained in each sub-layer can also be different from the drugs contained in any other sub-layer.

According to yet another embodiment of the present invention, a decrease in the release rate can be achieved by inducing the process of transformation of the amorphous portions of the polymer of the topcoat layer to a crystalline form. To cause crystallization of the amorphous fragments of the topcoat polymer, the topcoat can be heat-treated by annealing. The annealing can be performed by using, for example, hot air. The temperature used for heat treatment can be between about 130° C. and 150° C., for example, 140° C. The annealing cycles comprising between about 3 and about 7 seconds, for example, about 5 seconds of heating and about 10 to about 20 seconds, for example, about 15 seconds of keeping the heat off, can be used. The heat-treatment can include, for example, 10 annealing cycles.

As a result of the heat-treatment, the amorphous portions of the polymer forming the topcoat layer can crystallize and realign leading to tighter packing of the macromolecules. The amount of free space between the macromolecules and the rate of diffusion of the drug through the topcoat layer are reduced. Consequently, the rate of release of the drug is reduced.

According to another embodiment of the present invention, a finishing coat layer, if used, can include a therapeutically active agent or agents to provide the coating with additional medical benefits. Examples of suitable therapeutically active agents that can be incorporated in the finishing coat layer include poly(ethylene glycol) (PEG), heparin and hyaluronic acid. A brand of heparin known under the trade name DURAFLO can be used. DURAFLO can be obtained from Baxter Healthcare Corporation of Deerfield, Ill.

The coating of the present invention has been described in conjunction with a stent. However, the coating can also be used with a variety of other medical devices. Examples of the implantable medical device that can be used in conjunction with the embodiments of this invention include stent-grafts, grafts (e.g., aortic grafts), artificial heart valves, cerebrospinal fluid shunts, pacemaker electrodes, coronary shunts and endocardial leads (e.g., FINELINE and ENDOTAK, available from Guidant Corporation). The underlying structure of the device can be of virtually any design. The device can be made of a metallic material or an alloy, such as, but is not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

The polymer can be applied to the stent by dissolving the polymer in a solvent and applying the resulting composition on the stent or immersing the stent in the composition. Representative examples of suitable solvents include N,N-dimethylacetamide (DMAC), N,N-dimethylformamide (DMF), tethrahydrofurane (THF), dimethylsulphoxide (DMSO), or blends of these solvents with each other or with other solvents, for example, a blend of DMAC with ethanol.

The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

EXAMPLES

Some embodiments of the present invention are illustrated by the following Examples.

Example 1

A first composition can be prepared by mixing the following components:

(a) about 3.8 mass % of EVAL;

(b) about 0.2 mass % of EVEROLIMUS; and (c) the balance, DMAC solvent.

The composition can be applied onto stent a bare 13 mm TETRA stent (available from Guidant Corp.) by spraying and dried to form a drug-polymer layer. A spray coater having an EFD 7803 spray valve with 0.014 inch fan nozzle with a VALVEMATE 7040 control system, manufactured by EFD, Inc. of East Providence, R.I., can be used. The fan nozzle can be maintained at about 60° C. with a feed pressure of about 0.2 atm (about 3 psi) and an atomization pressure of about 1.35 atm (about 20 psi). The total amount of solids of the drug-polymer layer can be about 80 micrograms, including about 4 μg of EVEROLIMUS and about 76 μg of EVAL. "Solids" means the amount of the dry residue deposited on the stent after all volatile organic compounds (e.g., the solvent) have been removed. A primer (e.g., the above formulation without the therapeutically active compound) can be optionally applied on the surface of the bare stent.

A second composition comprising about 2.0 mass % of EVAL and the balance of DMAC can be prepared and applied onto the dried drug-polymer layer by spraying and dried, to form the topcoat layer. The topcoat layer can have a total solids weight of about 475 μg. A grade of EVAL having $M_w$ of about 206,000 (to be determined by the method of light scattering) and the PDI of about 2.8 can be used for making the topcoat layer.

Example 2

A stent can be coated as described in Example 1. The coating formed on the stent can be heat-treated by annealing. The annealing can be performed in cycles. Each annealing cycle includes treatment of the stent by directing to the topcoat a stream of hot air having a temperature of about 140° C. for about 5 seconds followed by turning off the heat for about 15 seconds. A total of ten such annealing cycles can be performed.

Example 3

A stent can be coated and annealed as described in Example 2. A composition can then be prepared, the composition including:

(a) between about 0.1 mass % and about 2.0 mass %, for example, about 1.75 mass % of EVAL;

(b) between about 0.1 mass % and about 2.0 mass %, for example, about 0.25 mass % of PEG;

(c) between about 0.1 mass % and about 2.0 mass %, for example, about 0.5 mass % of heparin, for example, DURAFLO; and (d) the balance, a solvent blend comprising about 80 mass % of DMAC and about 20 mass % of ethanol.

The composition can be applied onto the annealed topcoat layer to form a finishing coat layer.

Example 4

A first composition was prepared by mixing the following components:

(a) about 4.0 mass % of EVAL; and (b) the balance, a mixture of solvents, DMAC and ethanol, in a ratio of DMAC to ethanol of about 80:20 by mass.

The first composition was applied onto the surface of a bare 13 mm TETRA stent to form a primer layer. The primer layer was baked at about 140° C. for about one hour, yielding a primer layer with an average total amount of solids of about 160 µg.

A second composition was prepared by mixing the following components:

(c) about 4.0 mass % of EVAL;

(d) about 3.2 mass % of EVEROLIMUS; and (e) the balance, a mixture of solvents, DMAC and ethanol, in a ratio of DMAC to ethanol of about 80:20 by mass.

The drug-to-polymer (EVEROLIMUS:EVAL) ratio (mass) was about 1:1.25. The second composition was applied onto the dried primer layer to form a first drug-polymer sub-layer, followed by drying at about 50° C. for about 2 hours. The total amount of solids of the first drug-polymer sub-layer was about 331 µg.

A third composition was prepared by mixing the following components:

(f) about 4.0 mass % of EVAL;

(g) about 1.33 mass % of EVEROLIMUS; and (h) the balance, a mixture of solvents, DMAC and ethanol, in a ratio of DMAC to ethanol of about 80:20 by mass.

The drug-to-polymer (EVEROLIMUS:EVAL) ratio (mass) was about 1:3. The third composition was applied onto the dried first drug-polymer sub-layer to form a second drug-polymer sub-layer, followed by drying at about 50° C. for about 2 hours. The total amount of solids of the second drug-polymer sub-layer was about 50 µg.

The combination of the first and the second drug-polymer layers comprised an overall drug-polymer layer in which the drug-to-polymer ratio was about 1:1.4. Overall stent coating (i.e., the primer layer plus the two drug-polymer sub-layers) had the total amount of solids of about 543 µg and the drug-to-polymer ratio in the overall coating was about 1:2.4.

Examples 5–13

The stents were coated according to the process described in Example 4, where the weights of the two drug-polymer sub-layers and the drug-to-polymer ratios in the drug-polymer sub-layers varied as summarized in Table 1.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

TABLE 1

The Compositions of Examples 5–13

| | Drug-Polymer Sub-layer 1 | | Drug-Polymer Sub-layer 2 | | EVEROLIMUS-to-EVAL mass ratio for combined drug-polymer sub-layers | Total coating weight, µg | EVEROLIMUS-to-EVAL mass ratio for the overall coating |
|---|---|---|---|---|---|---|---|
| Example | Weight, µg | EVEROLIMUS-to-EVAL mass ratio | Weight, µg | EVEROLIMUS-to-EVAL mass ratio | | | |
| 5 | 191 | 1:1.25 | 300 | 1:3 | 1:2.07 | 651 | 1:3.07 |
| 6 | 338 | 1:1.25 | 50 | 1:4 | 1:1.43 | 548 | 1:2.43 |
| 7 | 338 | 1:1.25 | 300 | 1:4 | 1:2.99 | 798 | 1:3.99 |
| 8 | 360 | 1:1.25 | 50 | 0:1*) | 1:1.56 | 570 | 1:2.56 |
| 9 | 360 | 1:1.25 | 300 | 0:1*) | 1:3.13 | 820 | 1:4.13 |
| 10 | 338 | 1:1.25 | 50 | 1:4 | 1:1.43 | 548 | 1:2.43 |
| 11 | 191 | 1:1.25 | 300 | 1:4 | 1:2.07 | 651 | 1:3.07 |
| 12 | 349 | 1:1.25 | 50 | 1:9 | 1:1.49 | 559 | 1:2.49 |
| 13 | 293 | 1:1.25 | 300 | 1:9 | 1:2.71 | 753 | 1:3.71 |

*)No EVEROLIMUS was used in sub-layer 2 in Examples 8 and 9; the second sub-layer served as a topcoat.

What is claimed is:

1. A coating on an implantable medical device, the coating comprising poly(ethylene-co-vinyl alcohol) having a weight-average molecular weight between about 200,000 and about 250,000 Daltons and a polydispersity index between about 2.6 and about 3.0.

2. The coating of claim 1, wherein the implantable medical device is a stent.

3. The coating of claim 1, additionally comprising a therapeutic substance.

4. The coating of claim 3, wherein the therapeutic substance is selected from the group consisting of rapamycin, 40-O-(2-hydroxy)ethyl-rapamycin, 40-O-(3-hydroxy)propyl-rapamycin, 40-O-[2-(2-hydroxy)ethoxy]ethyl-rapamycin, and 40-O-tetrazole-rapamycin.

5. The coating of claim 1, wherein the coating comprises a first layer and a second layer disposed over the first layer, wherein the first layer includes a polymer and a therapeutic substance and the second layer includes the poly(ethylene-co-vinyl alcohol) having a weight-average molecular weight between about 200,000 and about 250,000 Daltons and a polydispersity index between about 2.6 and about 3.0.

6. The coating of claim 5, wherein the ratio between the therapeutic substance and the polymer in the first layer is between about 1:1 and about 1:25.

7. A coating on an implantable medical device, the coating comprising poly(ethylene-co-vinyl alcohol) having a polydispersity index between about 2.6 and about 3.0.

8. The coating of claim 7, wherein the implantable medical device is a stent.

9. The coating of claim 7, additionally comprising a therapeutic substance.

10. The coating of claim 9, wherein the therapeutic substance is selected from the group consisting of rapamycin, 40-O-(2-hydroxy)ethyl-rapamycin, 40-O-(3-hydroxy)propyl-rapamycin, 40-O-[2-(2-hydroxy)ethoxy]ethyl-rapamycin, and 40-O-tetrazole-rapamycin.

11. The coating of claim 7, wherein the coating comprises a first layer and a second layer disposed over the first layer, wherein the first layer includes a polymer and a therapeutic substance and the second layer includes the poly(ethylene-co-vinyl alcohol) having a polydispersity index between about 2.6 and about 3.0.

12. The coating of claim 11, wherein the ratio between the therapeutic substance and the polymer in the first layer is between about 1:1 and about 1:25.

13. A coating on an implantable medical device, the coating comprising a layer including a polymer having a polydispersity index between about 2.6 and about 3.0 and a therapeutic substance, wherein the ratio between the therapeutic substance and the polymer in the layer is between about 1:1 and about 1:25.

14. The coating of claim 13, wherein the implantable medical device is a stent.

15. The coating of claim 13, wherein the therapeutic substance is selected from a group consisting of rapamycin, 40-O-(2-hydroxy)ethyl-rapamycin, 40-O-(3-hydroxy)propyl-rapamycin, 40-O-[2-(2-hydroxy)ethoxy]ethyl-rapamycin, and 40-O-tetrazole-rapamycin.

16. The coating of claim 13, additionally comprising a second layer disposed over the layer, the second layer comprising poly(ethylene-co-vinyl alcohol) having a weight-average molecular weight between about 200,000 and about 250,000 Daltons or a polydispersity index between about 2.6 and about 3.0.

17. A method of coating a stent comprising forming a coating comprising a copolymer of ethylene and vinyl alcohol on the stent, the copolymer having a weight-average molecular weight between about 200,000 and about 250,000 Daltons and a polydispersity index between about 2.6 and about 3.0.

18. The method of claim 17, wherein the coating further comprises a layer including a polymer and a therapeutic substance incorporated therein.

19. The method of claim 18, wherein the therapeutic substance is selected from the group consisting of rapamycin, 40-O-(2-hydroxy)ethyl-rapamycin, 40-O-(3-hydroxy)propyl-rapamycin, 40-O-[2-(2-hydroxy)ethoxy]ethyl-rapamycin, and 40-O-tetrazole-rapamycin.

20. The coating of claim 1, further comprising a topcoat that includes poly(ethylene glycol), hyaluronic acid, heparin or a combination thereof.

21. The coating of claim 1, further comprising a topcoat treated by an annealing process.

22. The coating of claim 7, further comprising a topcoat treated by an annealing process.

* * * * *

UNITED STATES PATENT AND TRADEMARK OFFICE
CERTIFICATE OF CORRECTION

| | | |
|---|---|---|
| PATENT NO. | : 7,087,263 B2 | Page 1 of 1 |
| APPLICATION NO. | : 10/269004 | |
| DATED | : August 8, 2006 | |
| INVENTOR(S) | : Hossainy et al. | |

It is certified that error appears in the above-identified patent and that said Letters Patent is hereby corrected as shown below:

On the Title page, above the Inventor information change the title to read:

Item --(54)    RATE LIMITING BARRIERS FOR IMPLANTABLE MEDICAL DEVICES--.

On page 4, beginning of column 1, change the title to read:

--RATE LIMITING BARRIERS FOR IMPLANTABLE MEDICAL DEVICES--.

Signed and Sealed this

Fifteenth Day of May, 2007

JON W. DUDAS
*Director of the United States Patent and Trademark Office*